United States Patent
Clark, Jr.

(10) Patent No.: US 6,343,225 B1
(45) Date of Patent: Jan. 29, 2002

(54) IMPLANTABLE GLUCOSE SENSOR

(75) Inventor: Leland C. Clark, Jr., Cincinnati, OH (US)

(73) Assignee: Implanted Biosystems, Inc., Kettering, OH (US)

( * ) Notice: Subject to any disclaimer, the term of this patent is extended or adjusted under 35 U.S.C. 154(b) by 0 days.

(21) Appl. No.: 09/395,466

(22) Filed: Sep. 14, 1999

(51) Int. Cl.$^7$ .................................................. A61B 5/05
(52) U.S. Cl. ........................ 600/347; 600/365; 600/377
(58) Field of Search ................................ 600/309, 345, 600/347, 365, 377; 204/403, 415, 414; 435/14, 177

(56) References Cited

U.S. PATENT DOCUMENTS 5,431,160 A * 7/1995 Wilkins ...................... 600/347
6,081,736 A * 6/2000 Colvin et al. ........... 600/347 X

* cited by examiner

Primary Examiner—Eric F. Winakur
Assistant Examiner—Ryan Carter
(74) Attorney, Agent, or Firm—Crosby, Heafey, Roach & May

(57) ABSTRACT

The sensitivity of enzyme-based polarographic electrodes to oxygen concentration can be significantly reduced or eliminated by providing an oxygen-reservoir in intimate contact with the oxidative enzyme. This is achieved by making a stabilized emulsion between the enzyme and a compound in which oxygen is extremely soluble. An aqueous glucose oxidase solution is emulsified with a perfluorocarbon liquid, and the resulting emulsion is stabilized by chemically crosslinking the mixture to form a gel. Thin layers of the emulsion are fabricated by spreading a layer of the liquid emulsion before gelation occurs. Additional carrier proteins such as albumin may be added to the enzyme prior to crosslinking to protect enzymatic activity and enhance gel strength. Additional electron transport compounds may be added to further reduce sensitivity to oxygen concentration.

18 Claims, 10 Drawing Sheets

IMPLANTABLE GLUCOSE SENSOR

BACKGROUND OF THE INVENTION

1. Field of the Invention

The present invention concerns the field of electrochemical devices for detection and measurement purposes and more specifically an enzyme emulsion for use in an implantable miniature polarographic glucose sensor.

2. Description of Related Art

There is currently a considerable need for a glucose sensor that can be readily implanted into a human where it will function for a prolonged time period. The primary impetus for such a device is diabetes, a potentially devastating complex disorder of glucose metabolism, currently controllable through insulin injections, is increasing worldwide. In the United States it is estimated that over ten million persons have diabetes. The monetary cost to society is in the many billions of dollars reflecting treatment expense and loss of productivity while the human cost in impaired function, progression to blindness, limb amputations, kidney failure and heart and vascular disease is immeasurable.

It has been known for well over seventy years that this disease primarily results from inadequate secretion of the hormone insulin by the islet or Beta cells of the pancreas. When uncontrolled, this disease often leads to serious metabolic imbalances—elevated glucose levels lead to ketosis and to damaging alterations in blood pH while inadequate glucose levels lead to lethargy and coma. Diet and daily injections of insulin are now used in an attempt to control life-threatening swings in blood glucose. It is now well established that the damage is caused by excessive glucose and not directly by lack of insulin. Glucose combines with hundreds of proteins essential for normal metabolism and in that way damages the cellular machinery of the body.

Control of diabetes by insulin injection generally results in much wider swings in blood glucose level than are common in a normal individual. Occasional insulin injections (up to several per day) are unable to duplicate the strict control of blood glucose afforded by a properly functioning pancreas which continually meters out just enough insulin to maintain a stable and relatively normal blood glucose level. Extremes in blood glucose level need be avoided. Yet despite avoiding extremes in blood glucose level insulin-dependent diabetics suffer a host of other maladies, mentioned above, that decrease both the quality and length of life. Diabetics experience frequent vascular disease that often results in amputation of limbs as impaired circulation prevents adequate blood flow. Abnormal vascular growth within the eye may result in intraocular bleeding and retinal damage with progressive loss of vision. Nerve degeneration may lead to loss of sensation and other related problems.

To control the blood level of glucose by injection of insulin requires the analysis of six to eight samples of blood each day. This is usually performed by puncturing the finger tip with a small lancet and analyzing blood glucose level with a photometric "home glucose monitor." This is, of course, not a pleasant experience and requires considerable skill as well as motivation. As home glucose tests have became common, more and more data have became available demonstrating the relatively poor control of blood glucose afforded by periodic insulin injections. At the same time, a growing number of clinical studies demonstrated that strict control of blood glucose reduces many if not all of the diabetes-related diseases mentioned above. Many scientists and physicians now believe that greatly improved blood glucose control can largely eliminate the mortality and morbidity associated with diabetes.

The ultimate goal of diabetes treatment is a replacement for the patient's non-functioning pancreatic islet cells. Some scientists are seeking ways to transplant functioning islet cells into diabetic patients to provide a naturally controlled source of insulin. Other scientists are working on automatic insulin injection systems that deliver exogenously supplied insulin as needed to maintain precise blood glucose control. Most probably both of these "cures" will be needed. Although transplanted islet cells would seem to be the optimal solution, at this time anti-rejection drugs required for transplants have almost as many negative side effects as diabetes itself. In any case, a self-regulating artificial insulin source is needed to limit the damage caused by diabetes until islet transplantation is perfected. Even when transplantation is widely available, a self regulating insulin source will be needed for patient maintenance prior to transplantation, and, perhaps, for some post-transplantation support.

Many types of regulated injection systems, both implantable and external, are already available. The key problem continues to be the requirement for an accurate glucose sensor to control these injection systems. The need to continually monitor glucose levels to permit a constantly metered dispensing of insulin generally eliminates methods relying on blood samples. It is clear that an implantable glucose sensor that measures in vivo glucose levels is the real answer.

Previous to modem instrumentation the analysis for blood glucose required a venipuncture with the collection of several milliliters of blood, precipitation, filtration, treatment with a colorimetric glucose reagent and spectrophotometric determination of glucose. The invention of the first "enzyme electrode" and glucose sensor by the present inventor in the 1960's led to the production of the first commercially successful blood glucose analyzer. The Clark glucose sensor consisted of a platinum anode, a layer of glucose oxygen oxioreductase (glucose oxidase) and a cellophane or cellulose acetate membrane. A silver "reference" electrode was also incorporated into the sensor. Only 0.01 ml of blood was required and the final analysis was complete in about one minute. Since then literally billions of blood samples have been analyzed by this type of instrument.

The inventor's polarographic glucose method just mentioned is explained in U.S. Pat. No. 3,539,455. The chemical reaction most commonly used by such enzyme-coupled polarographic glucose sensors is glucose oxidase mediated catalytic oxidation of glucose by atmospheric oxygen to produce gluconolactone and hydrogen peroxide (equation 1):

$$C_6H_{12}O_6 + O_2 + H_2O \rightarrow C_6H_{12}O_7 + H_2O_2 \tag{1}$$

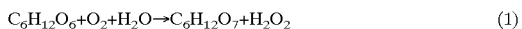

In the presence of excess oxygen, the quantity of hydrogen peroxide produced will be a direct measure of the glucose concentration. The hydrogen peroxide is measured by being reoxidized by an electrode (anode) maintained at an appropriate positive potential (equation 2):

$$H_2O_2 - 2e^- \rightarrow O_2 + 2H^+ \tag{2}$$

The glucose detection process, then, is dependent upon the measurement of electrons removed from hydrogen peroxide in equation (2). The electrode is normally formed from a noble metal such as gold or platinum. The latter preferred metal although carbon, pyrolytic or glassy, graphite and other electrically conducting materials are sometimes used.

As is well known to those of ordinary skill in the art, other specific hydrogen peroxide producing oxidase enzymes can be used to produce sensors for other substances such as cholesterol (cholesterol oxidase), amino acids (amino acid oxidase), alcohol (alcohol oxidase), lactic acid (lactate oxidase), and galactose (galactose oxidase), to name only a few.

The success of this kind of enzyme-based sensor suggested to many that a similar sensor might be implanted with a simple power source and a means for transmitting the glucose data to the outside of the body. Such a continuously reading device would not only eliminate the pain of repeatedly puncturing the finger but would also supply a constant reading of the glucose level. It is known that the glucose level in many locations in the body closely mirror the blood glucose level. Numerous attempts have been made to make such a device available to diabetics. However, experimental devices did not function a sufficiently long period of time. These failures of implanted glucose sensors were ascribed to diverse problems, many of which appeared to be without solution. For example, some believed that the hydrogen peroxide (and free radicals) generated by the oxidase reaction caused denaturation and inactivation of the oxidase enzyme. Another, more common, explanation was that the glucose sensor was "not compatible" with the human body or that the surface of the measuring tip of the electrode became coated with layers of scar-like tissue which not only impeded the diffusion of glucose but jeopardized or destroyed nearby capillaries. Others held that the platinum electrode surface became "poisoned" by body fluids. However, extensive studies of implanted platinum electrodes conducted in the inventor's laboratory over the last forty years have completely exploded the myth of the "poisoned" platinum surface. Some implanted platinum electrodes have remained functional for up to six years.

It is a goal of this invention to similarly deal with other impediments to successful implantable glucose sensors. Glucose is extremely soluble in biological fluids whereas oxygen is poorly soluble in these same fluids and must be carried by specialized biomolecules such as hemoglobin. Many tissues of the human body have an oxygen tension equivalent to between about 2–5% oxygen in nitrogen or lower. As a result, there may be a ratio of glucose to oxygen sometimes as high as 100 to 1 in subcutaneous interstitial and peritoneal fluids. This means that at the electrode surface there may be only 1% of the oxygen required for glucose oxidase to quantitatively oxidize the available glucose for measurement purposes.

Furthermore, the glucose oxidase in a glucose sensor must be protected from proteases and other macromolecules which might destroy or inhibit the glucose oxidase, from enzymes such as catalase which destroy hydrogen peroxide (catalase, dehydrogenases, etc.), from microbes which digest the enzymes and from soluble compounds, such as ascorbate and acetoaminophen, which interfere with the either the enzymatic or electrochemical reactions. This protection can be achieved by separating the glucose oxidase from biological fluids by a semipermeable membrane. The best known membranes that are capable of selectively excluding proteins such as catalase while allowing the entry of glucose are so-called dialysis membranes. These membranes are generally hydrophilic membranes containing "pores" that readily admit neutral molecules with molecular weights below about 5,000 Daltons. Common examples of these membranes are prepared from various regenerated celluloses such as cellophane, Spectrapore® or Cuprophan® (brands of regenerated cellulose), cellulose esters, and membranes of polycarbonate or polysulfone.

While such semipermeable membranes do a good job of excluding undesirable proteins as well as retaining the essential glucose oxidase, they also impede oxygen diffusion. Some membranes, however, such as those of polytetrafluoroethylene (Teflon® brand of perfluorocarbon resin) or of silicone rubber are permeable to oxygen, but these membranes are virtually impermeable to glucose, and hence, cannot be used to protect an oxygen requiring glucose sensor. U.S. Pat. No. 5,322,063 to Allen et al. reports a new type of polyurethane membrane said to allows some glucose permeability while favoring oxygen permeability.

Because of a superabundance of glucose and a shortage of oxygen, an implanted glucose sensor will tend to be oxygen limited and, thus, effectively measure oxygen instead of, or together with, glucose. That is, under ideal conditions when the glucose concentration is low, oxygen would be adequate so that an increase in glucose concentration would result in a concomitant and proportional increase in hydrogen peroxide and, therefore, measured current at the electrode. However, as the concentration of glucose increases, oxygen ultimately becomes insufficient causing the measured current to plateau regardless of glucose concentration. Above this plateau changes in the current reflect changes in oxygen tension (concentration) rather than in glucose concentration.

Many workers have failed to take into account the high glucose to oxygen ratio of human tissues. There are at least two ways to solve this problem: one can attempt to reduce the concentration of glucose that reaches the glucose sensor and/or one can attempt to increase the amount of oxygen available at the glucose sensor. The level of glucose can be reduced either by providing a permeability barrier to glucose or by providing additional, non-peroxide generating enzyme systems, such as dehydrogenases, besides glucose oxidase, to consume excess glucose. The polyurethane membrane mentioned above is an example of glucose restriction.

The second approach involves an attempt to increase the level of available oxygen or to maximize the availability of oxygen to the oxygen-requiring enzymes. The present inventor has previously disclosed methods for increasing the oxygen level in U.S. Pat. Nos. 4,680,268 and 4,721,677, which are hereby incorporated by reference. These patents teach the use of an oxygen-collecting chamber made of an oxygen permeable material such as silicone rubber. This chamber is separated from the oxygen-requiring enzyme by an oxygen permeable membrane. The chamber collects oxygen and delivers it by diffusion to the enzyme mixture near the measuring electrode. These patents also disclose filling the oxygen-collecting chamber with an oxygen-dissolving compound such as a perfluorocarbon liquid for speeding diffusion of oxygen to the oxygen-requiring enzyme. Alternatively, an emulsion of a perfluorocarbon liquid and the enzyme solution could be used to fill the chamber with the device configured so that the emulsion flows slowly onto the electrode, supplying oxygen and replenishing the enzyme. A recent publication (Wang and Lu, J. American Chem. Soc. 120:1048–50(1998)) adopts this liquid emulsion strategy but add graphite or carbon powder so the emulsion also functions directly as an electrode. This could cause difficulties with an implantable electrode since macrophages might react to the carbon powder.

Experiments in the inventor's laboratory have also showed that the current output from chronically implanted sensors can be used to control ascorbic acid levels in the brain using a feedback loop to an ascorbate pump and connected indwelling catheter. Further, it has been shown that polarographic anodes can be used quantitatively to measure blood flow in the vicinal capillary beds. It has been found from thousands of hours or continuous recording, that the oxygen available to the surface of an implanted oxygen sensor, and therefore to the glucose sensor described herein, is not steady but waxes and wanes in waves of six to eight cycles per minute. In some cases the amplitude of this variation can be plus or minus 30%. Buffering such fluctuation in available oxygen would be highly desirable in an oxygen-requiring glucose sensor since the functioning of such sensors depends upon oxygen.

In glucose sensor longevity experiments in the inventor's laboratory using sensors implanted in the peritoneal space of mice it was found that some sensors retained full activity for over 400 days. Over time the activity of most sensors gradually declined. These data demonstrated that adequate longevity could be achieved but that some factor, perhaps mechanical, frequently caused loss of activity. The invention disclosed herein is designed to avoid microbial degradation of the enzyme as well as to resist attacks by free radicals, proteases and the host's immune system.

SUMMARY OF THE INVENTION

The present inventor has discovered that "oxygen sensitivity" of enzyme-based polarographic electrodes can be significantly reduced or eliminated by providing an oxygen-reservoir in intimate contact with the oxidative enzyme. This is achieved by making a stabilized emulsion of the enzyme and a compound in which oxygen is extremely soluble. For example, an aqueous glucose oxidase solution can be emulsified with a perfluorocarbon liquid and the resulting emulsion stabilized by chemically crosslinking the mixture to form a gel. Thin layers of the emulsion ideal for placing into contact with a noble metal electrode can be fabricated by spreading a layer of the emulsion prior to crosslinking. Additional carrier proteins such as albumin can be added to the oxidase prior to crosslinking to protect enzymatic activity from the crosslinking reagent.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide perfluorocarbon-containing enzymes or insolubilized enzyme emulsions for use in a miniature implantable sensor based.

The present invention is directed towards a fluorocarbon-containing enzyme suspension or emulsion. Although such an emulsion can be advantageously used in a variety of implantable electrodes, it is especially useful in a miniature implantable device described in copending applications Ser. Nos. 08/769,863 and 08/779,304, which are incorporated herein by reference.

Figure 1:
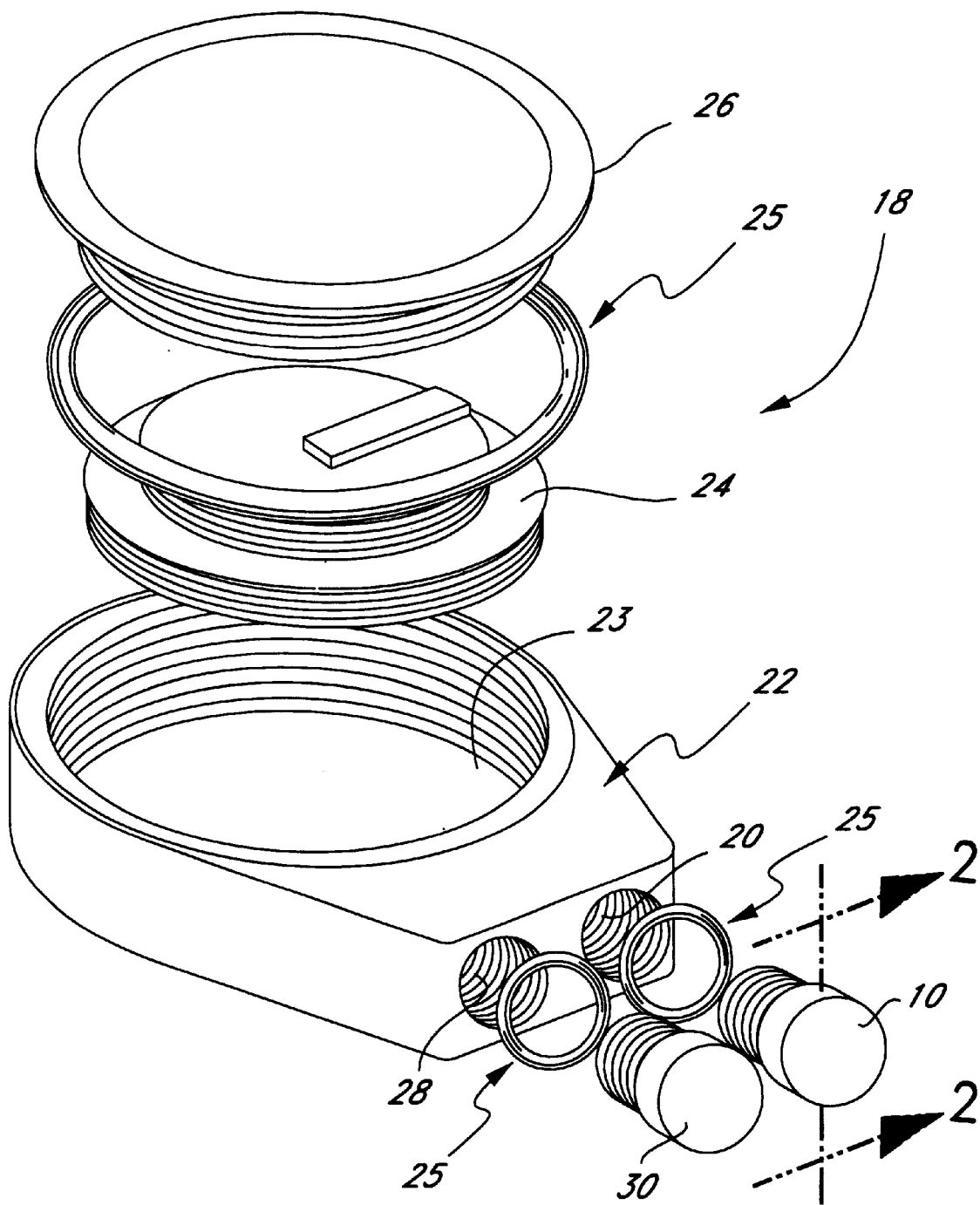
FIG. 1 illustrates diagrammatic view of a glucose sensor of the current invention.
Figure 2:
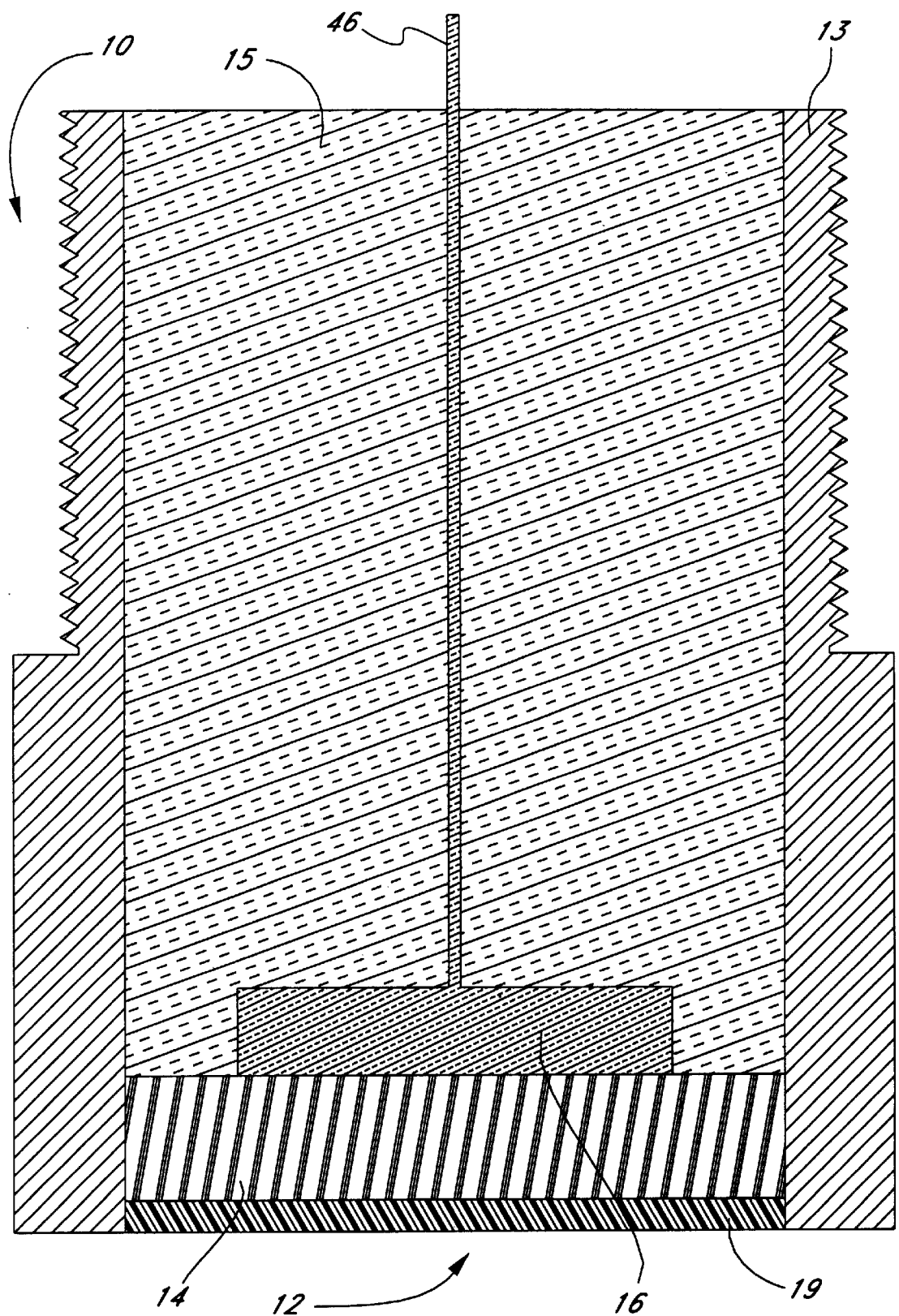
FIG. 2 illustrates an cross-sectional view of a working electrode of the device of FIG. 1.

As disclosed in the above-cited copending applications, a working implantable sensor of the glucose oxidase polarographic type can be readily constructed having a volume not much greater than a United States quarter. The overall shape of such an implantable sensor 18, as shown in FIG. 1, may be disc shaped although many other configurations are also possible. A case 22 contains a cavity 23 holding a printed circuit board 24 and is closed by a top 26 sealed by an O-ring 25. The case 22 also contains a first openings 28 for a reference electrode 30 and a second opening 20 for a working electrode 10. As shown in FIG. 2, the working electrode 10 of the device comprises an outer shell 13 with an opening 12 through which an enzyme mixture 14 along with an underlying electrode 16 contacts the body fluids. The electrode 16 can conveniently be made from platinum although a variety of other conductive materials are also useable. A conductor 46 connects the electrode 16 with the circuit board 24. Most of the shell 13 is filled with insulating glass or plastic 15 through which the conductor 46 passes. The enzyme mixture 14 is covered by a semipermeable membrane 19 to protect the enzymes from proteases, interfering substances, and attack by microbes and/or their oxidase destroying enzymes or other products. This membrane 19 is selected to be permeable both to glucose and to oxygen. The actual working tip of this electrode could be as small al 10 μm in diameter. Generally, the area occupied by the opening 12 is small as compared to the surface area of the device 18 constituting as little as 1% of the total surface area. Preferably, the device is implanted beneath the surface of the skin with the opening 12 facing towards the underlying layer of muscle. This position allows ready access to the unit for repair or replacement. The device can also be implanted so that the opening 12 contacts the peritoneal cavity. Generally the device is not directly in contact with the circulatory system so that formation of blood clots does not interfere with operation. All of the body tissues come into glucose equilibrium with the blood fairly rapidly so that placement of the device in contact with the blood is not really required.

Many researchers working on implantable glucose sensors may not understand or appreciate the importance of in situ sensor calibration. Both the enzyme mixture and the measuring electrode may change with time. Also, the microcirculation around the sensor may change so that the effective concentration or tension of oxygen changes. Unless the enzyme mixture response has the same slope at all possible oxygen concentrations, this could significantly change the accuracy of the glucose measurements. Many common laboratory instruments are calibrated by being exposed to analytes with known concentrations after which the instrument's output is adjusted to match the known analyte amount. Unfortunately, it is not possible to easily expose an implanted sensor to a known concentration of glucose.

However, considering that the implanted sensor is measuring a body compartment that is in equilibrium with the blood, blood glucose measurements can be used to effect calibration. If the patient or technician takes a series of blood glucose measurements over time, these can be plotted against sensor output to develop a time constant for sensor response. Thereafter, manual blood glucose measurements can be used to automatically calibrate or adjust the implanted sensor. The present inventor has also disclosed methods to use a single electrode to measure both oxygen and hydrogen peroxide (see U.S. Pat. No. 5,030,333 which is incorporated herein by reference). This provides a way to automatically adjust the sensors output where the enzyme mixture response shows a varying slope depending on oxygen concentration as well as providing knowledge of oxygen availability at the electrode.

As already mentioned, oxygen is relatively poorly soluble in biological fluids, and the membrane 19 that covers the opening 12 of the glucose sensor 10 is generally not very permeable to oxygen. However, it is also true that most of the cells of the human body require oxygen to function and in health receive an adequate supply. Although oxygen is not very soluble in biological fluids, it is highly "soluble" in the red blood cells by forming weak bonds with hemoglobin. These oxygen rich cells circulate in close proximity of virtually all of the body's cells so that the necessary oxygen can diffuse across the oxygen barrier (biological fluids and cell membranes) between the red blood cell's hemoglobin and an oxygen-requiring site such as a tissue cell.

The speed of oxygen diffusion through a barrier is controlled by the thickness of the barrier and by the amount of oxygen that can dissolve in a unit thickness of the barrier. That is, making the barrier thinner, or making the barrier dissolve more oxygen will increase the rate of oxygen diffusion. Therefore, the enzyme mixture 14 and the membrane 18 should be made as thin as feasible to maximize the rate of oxygen movement into the glucose sensor 10.

The present inventor has taken a novel approach to increasing the solubility of oxygen in the "barrier" of the glucose sensor 10. Various perfluorochemical liquids are widely known to dissolve relatively large amounts of oxygen. The present inventor's patents (U.S. Pat. Nos. 4,105, 798; 4,110,474; 4,187,252; 4,289,499; 4,443,480; RE33, 451; 5,514,720; 5,635,539; 5,684,050; 5,674,913; 5,824, 703; and 5,840,767) on the use of perfluorocarbon chemicals as emulsions and blood substitutes are incorporated herein by reference. There are a very large number of suitable perfluorocarbon liquids including those described in experiments below. The list comprises, but is not limited to, perfluorooctyl bromide, perfluorodichlorooctanes, perfluorodecalin, perfluoroindane, perfluorophenanthrene, perfluorotetramethylcyclohexane, perfluoropolyalkylether oil, perfluoromethyldecalin, perfluorodimethylethylcyclohexane, perfluorodimethyldecalin, perfluorotrimethyldecalin, perfluoroisopropyldecalin, perfluoropentamethyldecalin, perfluorodiisopropyldecalin, perfluorodiethyldecalin, perfluoromethyladamantane, perfluorodimethyladamantane, perfluoro-di-xylethane (mixed isomers), and perfluoro 6,7 H-undec-6-ene. Perfluorocarbon liquids are virtually insoluble in aqueous solutions, and proteins such as glucose oxidase are completely insoluble in perfluorocarbon liquids. Besides perfluorocarbons hydrocarbon drugs (e.g., cortical steroids) silicones, silanes, cyclic silanes, siloxanes, fluorinated silicones and other similar organo-silicon compounds are excellent oxygen solvents and are useful in the present invention. Besides dissolving oxygen and acting like as an oxygen reservoir, the most preferred compounds do not dissolve hydrogen peroxide. Thus, the hydrogen peroxide concentration and the responsiveness of the sensor is effectively increased. The particles of these compounds act as stepping stones for oxygen to reach the electrode surface.

However, it is known that relatively stable emulsions can be produced using perfluorocarbon liquids and aqueous solutions. When glucose oxidase, or other hydrogen peroxide-forming enzymes, are incorporated into the aqueous phase of such an emulsion, the perfluorocarbon serves as a pathway for oxygen to reach the enzyme as well as a reservoir of available oxygen. Further, it is possible to stabilize both the emulsion and the enzyme by treating the composition with a cross-linking agent such as an aldehyde similar to glutaraldehyde to chemically cross-link proteins into a gel. Tiny perfluorocarbon droplets are then enmeshed permanently by a cross-linked protein gel. Because the vapors of these perfluorocarbons are virtually insoluble in proteins or water, they are expected to remain in place for years. When amounts of enzyme below about 20% are used, the strength of this gel can be significantly increased by incorporating a relatively high concentration of additional carrier proteins into the emulsion to provide additional sites for reaction with the crosslinking reagents. Besides the aldehyde-based crosslinking agents, such as glutaraldehyde, a number of other effective protein crosslinking agents are well known in the art including carbodiimides, pyrocarbonates (i.e., diethyl pyrocarbonate), imidoesters, N-hydroxysuccinimid esters and multifunctional epoxides (i.e., polyethylene glycol diglycidyl ether).

The present invention, then, provides a greatly improved sensor by producing a cross-linked gel containing glucose oxidase or similar hydrogen peroxide-producing enzymes, an emulsified oxygen binding/permeable material, such as a perfluorocarbon, a silicone oil, a fluorosilicone oil, an aliphatic oil or organic compound such as a steroid, to carry oxygen to the enzyme, additional gelling agents, buffers and optional additives such as other enzymes and/or preservatives. Essentially, tiny solid or liquid particles of a material that readily dissolve oxygen are held in intimate contact with an oxygen utilizing enzyme which is preferably in an insoluble form.

The action of this emulsified oxygen carrier is two-fold. On one hand it holds oxygen and brings it into intimate contact with the enzyme to accept electrons from the enzyme. Because this substance is oxygen permeable it necessarily raises the effective oxygen concentration at the electrode and allows for more rapid diffusion of oxygen from a source such as the human circulatory system. At the same time the oxygen carrier effectively lowers the glucose level because it replaces a significant aqueous volume in which glucose is very soluble with an oxygen carrying volume in which glucose is extremely poorly soluble. That is, the glucose/oxygen ratios can be adjusted by increasing the hydrophobic oxygen carrier phase at the expense of the hydrophilic glucose-dissolving phase.

It is also contemplated that the oxygen permeable particles could comprise tiny gas bubbles (trapped bubbles as in a foam) produced by incorporating relatively high vapor pressure perfluorocarbon liquid into a protein-containing gel emulsion. Over time the perfluorocarbon would vaporize to form gas bubbles which remain trapped within the gel. These bubbles would hold a considerable supply of oxygen, and gaseous diffusion within the bubbles would be more rapid than diffusion within a liquid particle of the same size.

Following is a general method for preparation of stabilized enzyme mixtures according to the present invention. If the stabilized gel is to be based on a cross-linked protein gel, a suitable soluble carrier protein, such as an albumin, i.e., bovine serum albumin (BSA), or human serum albumin (HSA), or gelatin, at about 1 to 15% by weight final concentration is dissolved in a suitable buffer such as 0.2M sodium acetate buffer (pH 5.0), and a hydrogen peroxide producing enzyme such as glucose oxidase is dissolved in the mixture at about 1% to 5% by weight final concentration. While the examples presented use relatively low levels of glucose oxidase, embodiments using concentrations of 70% or greater glucose oxidase are also effective. At such high levels it is generally unnecessary to add albumin or other proteins to aid in gel formation.

Sufficient purified glutaraldehyde as an aqueous 2.5% solution is added to dilute the protein solution to the correct final concentration. The final glutaraldehyde concentration following dilution is preferably between 0.1 and 1% and more preferably about 0.6%. This mixture is swirled briefly to mix and is then poured onto a glass plate and spread with a glass rod. Aldehyde vapors can also be used to induce crosslinking. Within a few hours a uniform layer of enzyme gel is formed. This gel can be stored at 4° C. in a humidified atmosphere to prevent dehydration of the gel.

To incorporate an oxygen dissolving substance such as a perfluorocarbon liquid, a suitable amount of the oxygen dissolving liquid (usually between about 5% and 20% by volume) is added to the protein mixture and sonicated for two 15 second intervals while being maintained on ice. After the sonication, glutaraldehyde is added and the material is treated as above. The resulting gel may be stored in an atmosphere saturated with water and perfluorocarbon vapors to prevent evaporation of the perfluorocarbon. An alternate method of preparation is to add the active glucose utilizing enzymes to the sonicated BSA-perfluorocarbon emulsion prior to the glutaraldehyde addition to avoid possible denaturation of the enzyme during sonication.

Figure 3:
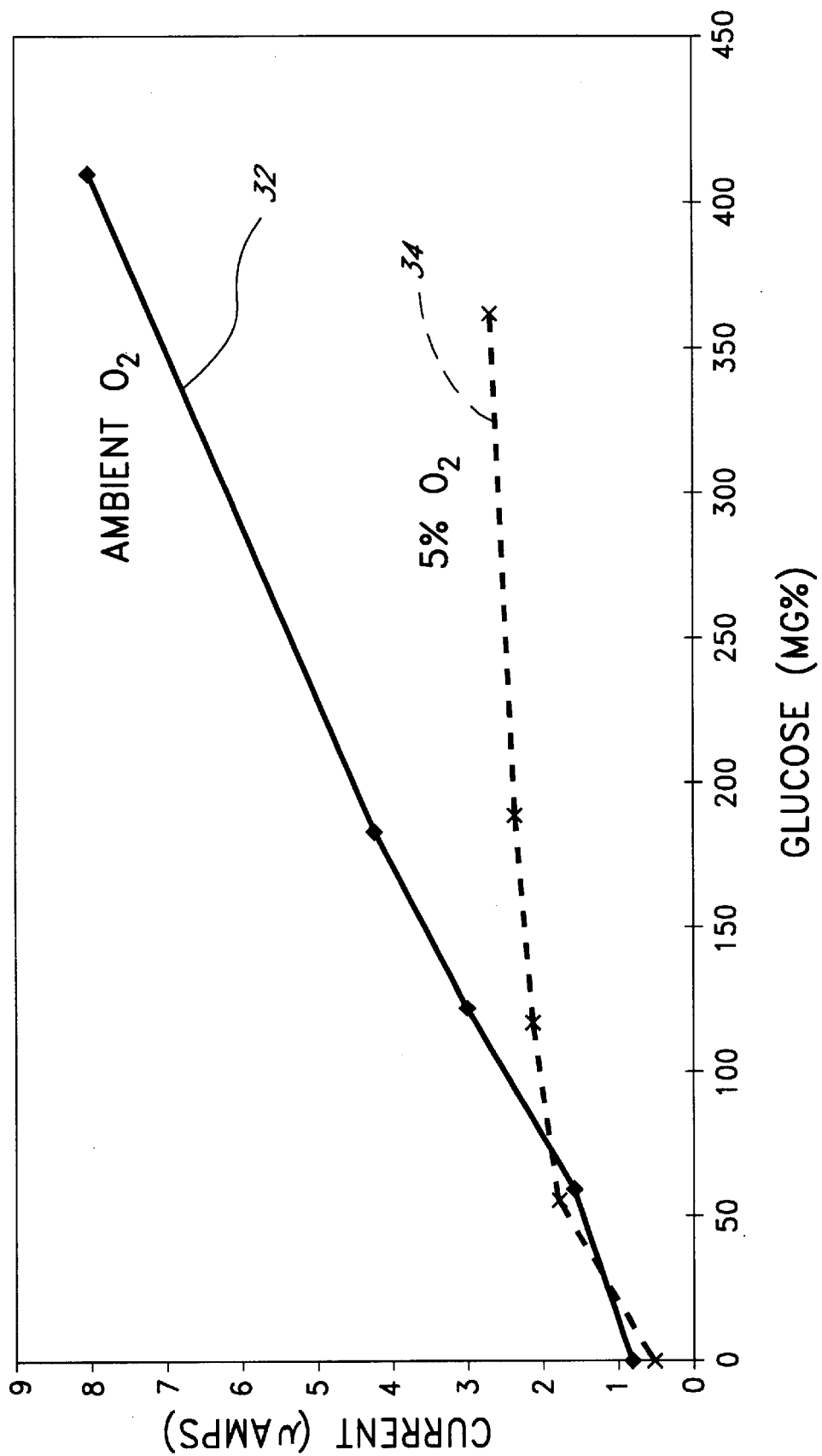
FIG. 3 shows the response of a stabilized enzyme mixture to varying glucose concentrations with ambient or with 5% oxygen.

To use the gel prepared as above a small piece is placed over a platinum electrode and covered with a piece of a Cuprophan® (brand regenerated cellulose) membrane. Alternatively, the gel can be divided into numerous small particles, and a slurry of these particles can be placed on the electrode surface and covered by the membrane. An additional variation is to paint the fluorocarbon-enzyme emulsion onto a membrane before the crosslinking agent has caused the mixture to "set." FIG. 3 shows the response of an ordinary stabilized enzyme mixture electrode to a range of glucose concentrations in either ambient (about 20%) or in 5% oxygen. An enzyme mixture was prepared according to the above method and contained about 2% glucose oxidase in an about 4% BSA gel stabilized with about 0.6% glutaraldehyde. Note that an ambient oxygen trace 32 shows an approximately linear response to at least a glucose concentration of 400 mg % (0.4%). On the other hand, a 5% oxygen trace 34 plateaus above about 50 mg % glucose indicating that oxygen is limiting the reaction.

It has been discovered that the concentration of BSA relative to glucose oxidase is may be important for producing higher and/or more stable signals. However, these factors do not appear to greatly affect the glucose concentration at which a sensor plateaus because of oxygen limitation. Because an implanted glucose electrode is expected to experience low oxygen tensions, the goal is to produce electrode response that is largely oxygen independent, or that at least produces a near linear response at low oxygen tensions.

Figure 4:
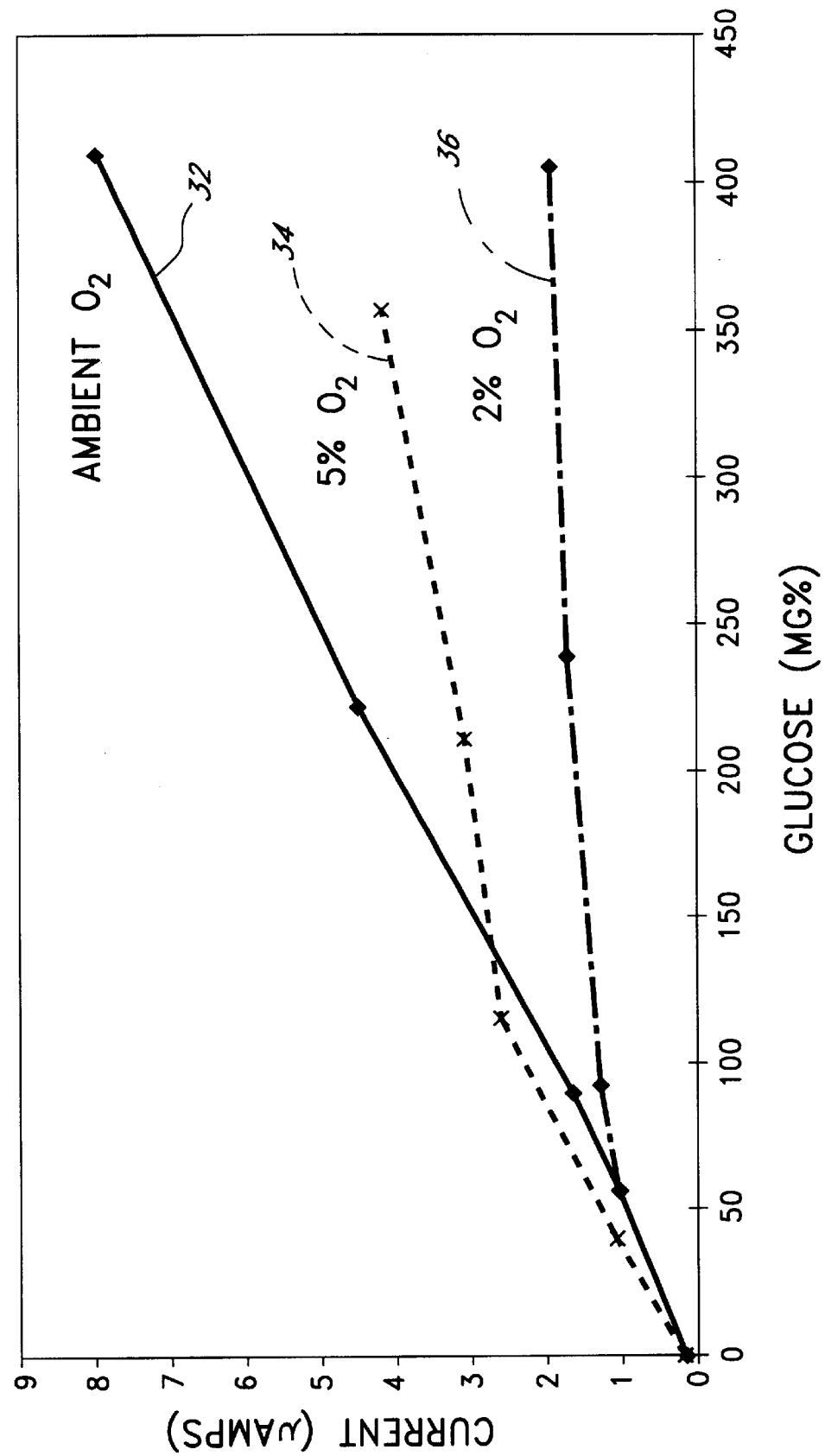
FIG. 4 shows the response of a stabilized enzyme emulsion containing about 7.5% Krytox brand of liquid perfluorocarbon to varying glucose concentrations with ambient or with 5% oxygen.

FIG. 4 illustrates the effect of adding an emulsified perfluorocarbon liquid to the stabilized enzyme mixture. The mixture in this case contains about 13% BSA, about 3% glucose oxidase and about 7.5% of emulsified Krytox® (brand of perfluoropolyalkylether synthetic oil, product of du Pont de Nemours) perfluorocarbon crosslinked with about 0.6% glutaraldehyde. The intent is for the perfluorocarbon to act as an oxygen source for the enzyme reaction. Because the perfluorocarbon is emulsified into tiny particles, there is an intimate association between the oxygen carrying perfluorocarbon and the oxygen-requiring enzyme. This limits the distance that oxygen must diffuse through a poor oxygen carrier such as water. With the perfluorocarbon acting as an oxygen source adequate enzyme response can occur even at low oxygen tensions.

In FIG. 4 the ambient oxygen trace 32, as before, is linear to at least 400 mg % glucose. However, the 5% oxygen trace 34 is now linear to at least 100 mg % glucose. Above this glucose concentration the slope of the response changes, but the electrode continues to show increasing response to over 350 mg % glucose. The electrode even shows some response at a very low oxygen concentration of 2% oxygen as is shown in a third trace 36.

Experiments with a large range of different perfluorocarbons have indicated that the amount as well as the type of perfluorocarbon can have a significant influence on the efficacy of the stabilized enzyme-perfluorocarbon mixture. Because the perfluorocarbon dissolves neither $H_2O_2$ nor $H_2O_2$ vapor, the response to small changes is faster. Generally, mixtures containing at least 15% by volume perfluorocarbon give better results. Also, perfluorocarbons with higher boiling points (lower vapor pressures) generally appear more effective. It is likely that there is a significant evaporative loss of lower boiling point perfluorocarbons (especially those with a boiling point below about 50° C.). This loss could significantly decrease the amount of perfluorocarbon available to act as an oxygen source/conductor.

Figure 5:
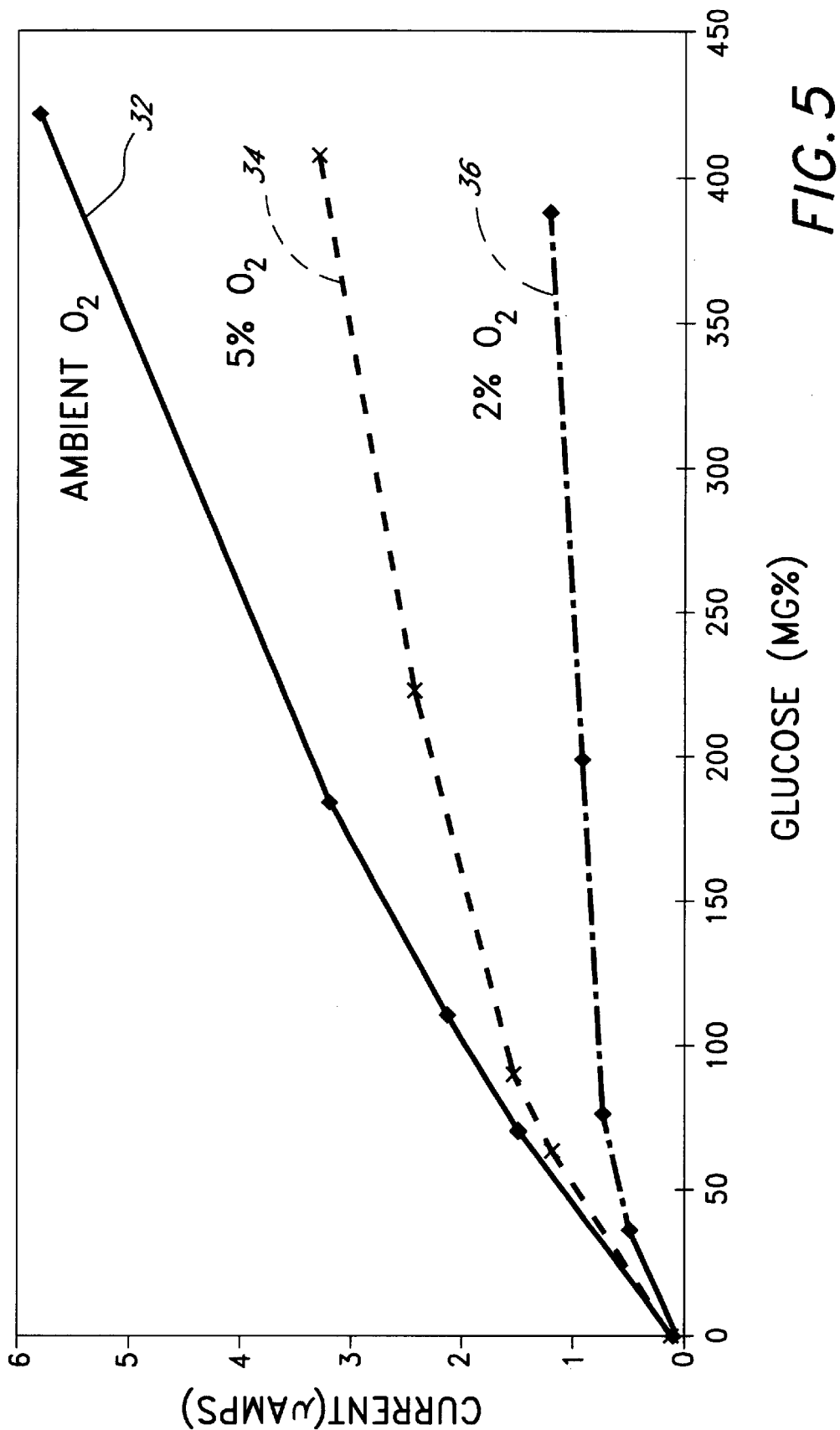
FIG. 5 shows the response of a stabilized enzyme emulsion containing about 15% AP200 fluorocarbon to varying glucose concentrations with ambient or with 5% oxygen.
Figure 6:
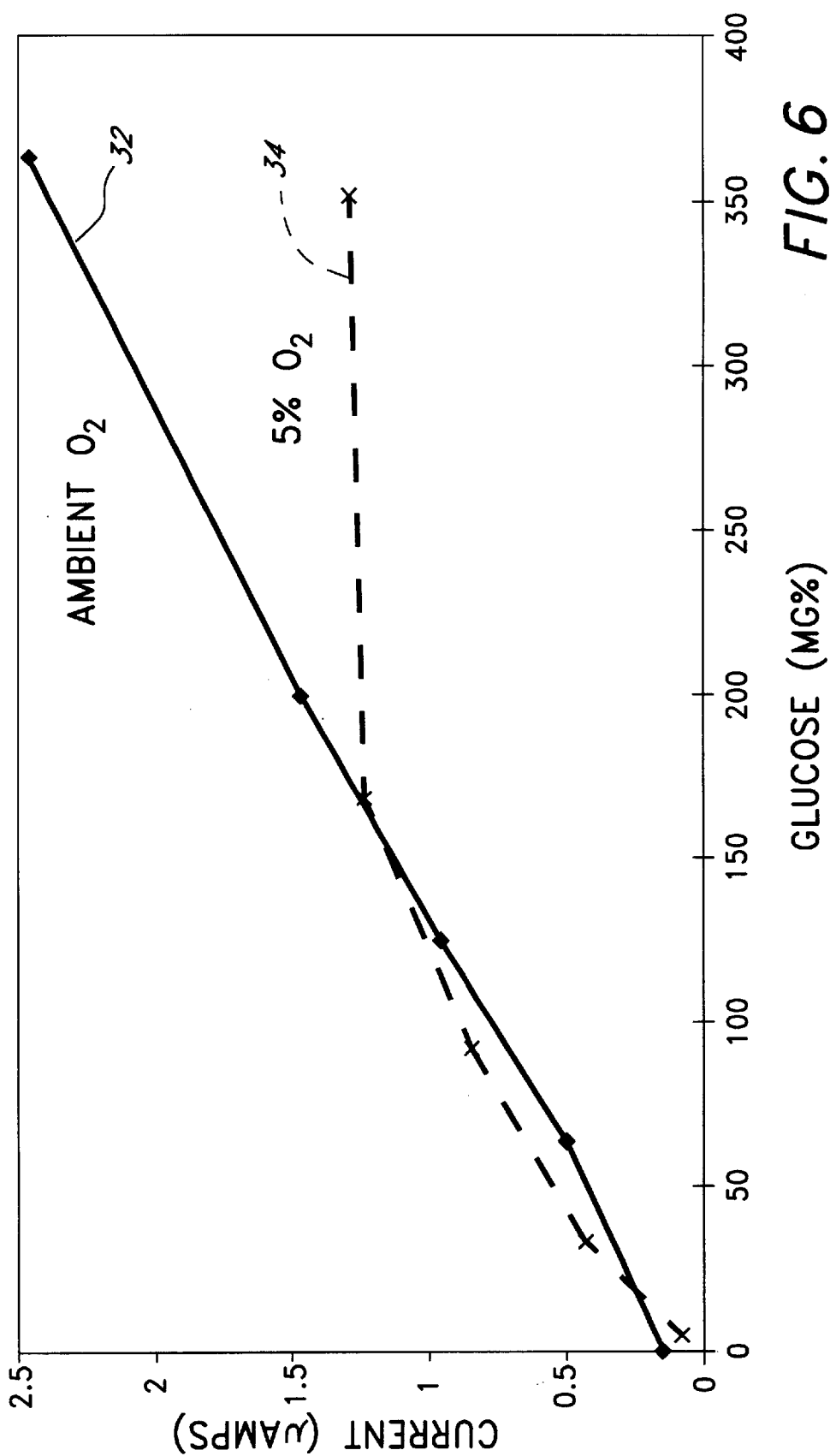
FIG. 6 shows the response of a stabilized enzyme emulsion containing about 7% AP200 fluorocarbon to varying glucose concentrations with ambient or with 5% oxygen.

FIG. 5 shows the results of a stabilized enzyme emulsion containing about 12% BSA, 4% glucose oxidase, 15% AP200 perfluorocarbon (mixed trimethyl and/or isopropyl perfluoro-decalins) (boiling point approximately 200° C.) crosslinked with 0.6% glutaraldehyde. In this case both the ambient oxygen trace 32 and the 5% oxygen trace 34 show relatively linear responses to above 350 mg % glucose although the slopes of the responses are somewhat different. The 2% oxygen trace 36 shows a very shallow response. These results should be compared with FIG. 6 where the enzyme emulsion contains only about 7% AP200. Note that the 5% oxygen trace 34 plateaus at about 150 mg % glucose when the lower concentration of perfluorocarbon is used.

Figure 7:
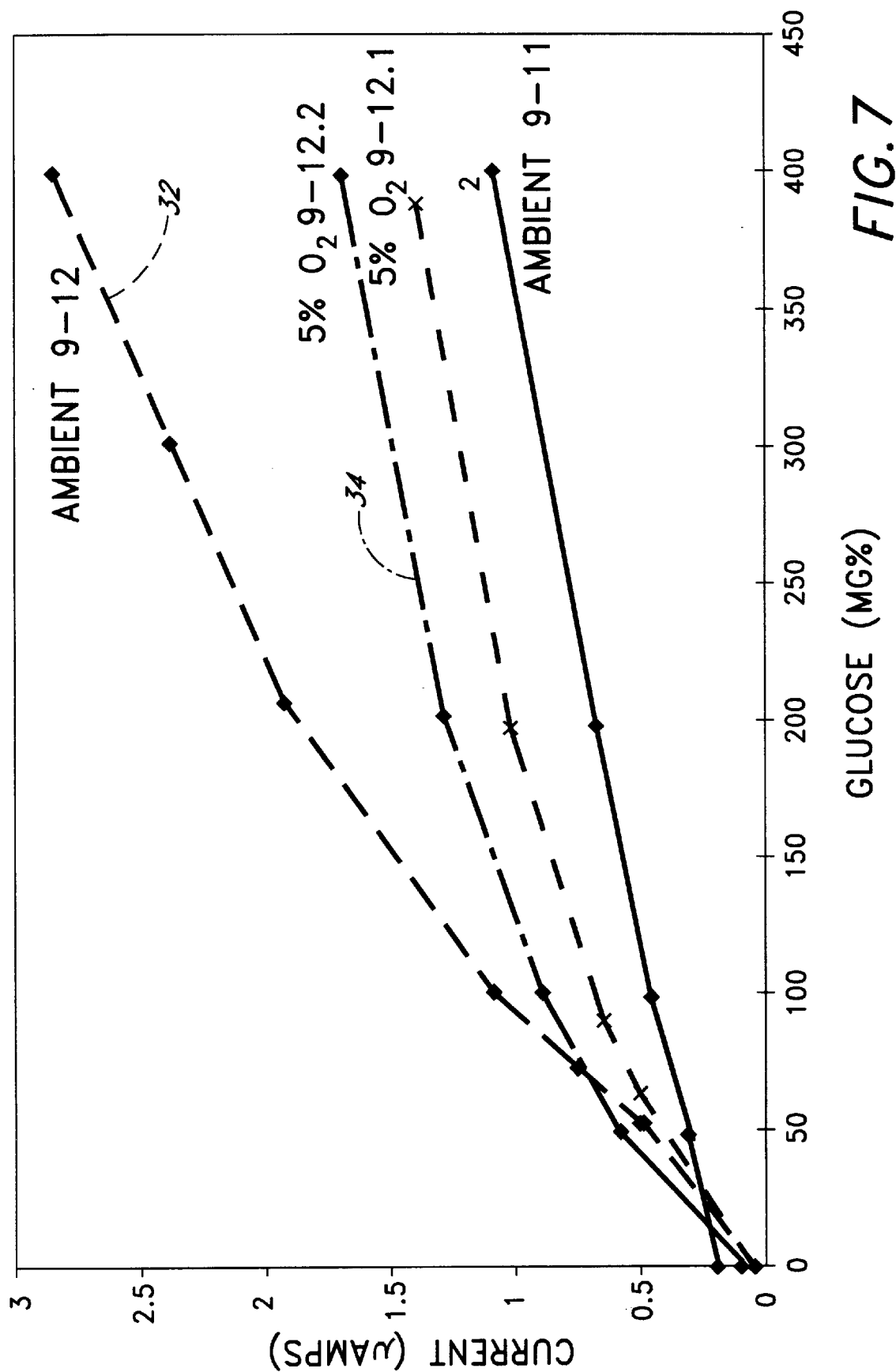
FIG. 7 shows the response of a stabilized enzyme emulsion containing about 37% AP215 fluorocarbon to varying glucose concentrations with ambient or with 5% oxygen.

FIG. 7 illustrates the results obtained from an emulsion similar to that of FIG. 5 except that 37% perfluorophenanthrene (AP215) (boiling point approximately 215° C.) is used in place of the AP200. The results are very similar to those of FIG. 5 indicating that there is probably little benefit to greatly increasing the quantity of perfluorocarbon beyond about 15%. As the amount of perfluorocarbon is increased, the overall signal decreases.

Figure 8:
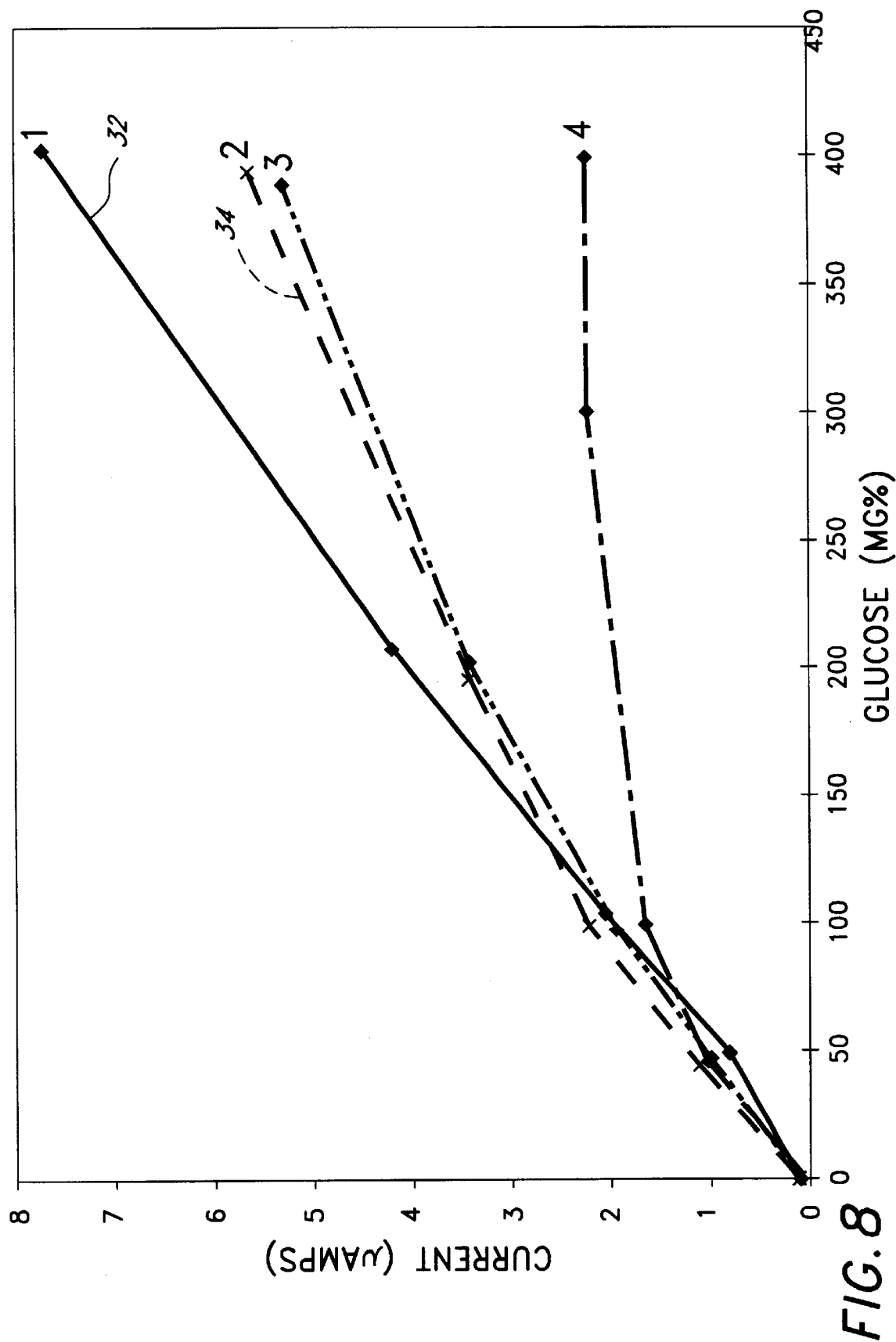
FIG. 8 shows the response of a stabilized enzyme emulsion containing about 15% AP240 fluorocarbon to varying glucose concentrations with ambient or with 5% oxygen.

As mentioned above, there is some indication that there is a benefit to using an even higher boiling perfluorocarbon. FIG. 8 shows the results of a stabilized enzyme emulsion containing about 15% AP240 (mixed pentamethyl and/or diisopropyl perfluoro-decalins) perfluorocarbon (boiling point approximately 240° C.), 10% BSA, 3% glucose oxidase and 0.6% glutaraldehyde. The AP240 was emulsified with the aid of 0.75% (final concentration) Pluronics F-68 brand emulsifying agent. A number of other emulsifying agents suitable for producing stable perfluorocarbon emulsions are well known in the art and can readily is used in the present invention. In addition, 0.75% glucose was added to protect the active site of glucose oxidase during cross-linking reaction. The comparison of the ambient oxygen trace 32 with the 5% oxygen trace 34 shows that this preparation is somewhat more active than the preparation illustrated in FIG. 5.

Inspection of Equations (1) and (2) show that the sensor indicates the rate of glucose oxidation (proportional to glucose concentration) by measuring removal of electrons from hydrogen peroxide at the electrode. When the enzyme oxidizes a molecule of glucose, an electron is removed from the glucose and accepted by a cofactor within the enzyme. Reacting with oxygen, which accepts an electron from the enzyme cofactor to produce hydrogen peroxide, regenerates the enzyme. At the surface of the electrode the electron is removed from the hydrogen peroxide thus regenerating oxygen. The electron flows through the circuit and is measured as a current. Thus, the hydrogen peroxide merely acts as an electron carrier to move electrons from glucose (by way of glucose oxidase) to the electrode.

It is also possible to use alternative electron carriers to move electrons from the reduced cofactor in glucose oxidase to the electrode surface. In theory any of a number of artificial electron carriers with the correct redox (reduction/oxidation) potential can perform the role of oxygen and hydrogen peroxide, thus rendering the entire reaction oxygen insensitive. Possible electron carriers include indophenol dyes, methyl viologen dyes, and various organometallic compounds. A presently preferred electron carrier for use with glucose oxidase is ferrocene (dicyclopentadienyliron) and its derivatives in which iron acts as the actual electron carrier. In proper formulations ferrocene can carry enough electrons from glucose oxidase to the electrode surface that the glucose oxidase reaction becomes independent of oxygen (i.e., can occur anaerobically). Ferrocene is virtually insoluble in aqueous solutions, and while ferrocene is soluble in some organic solvents, these solvents are generally not suitable for use in an implantable electrode. However, ferrocene is somewhat soluble in certain perfluorocarbons.

Figure 9:
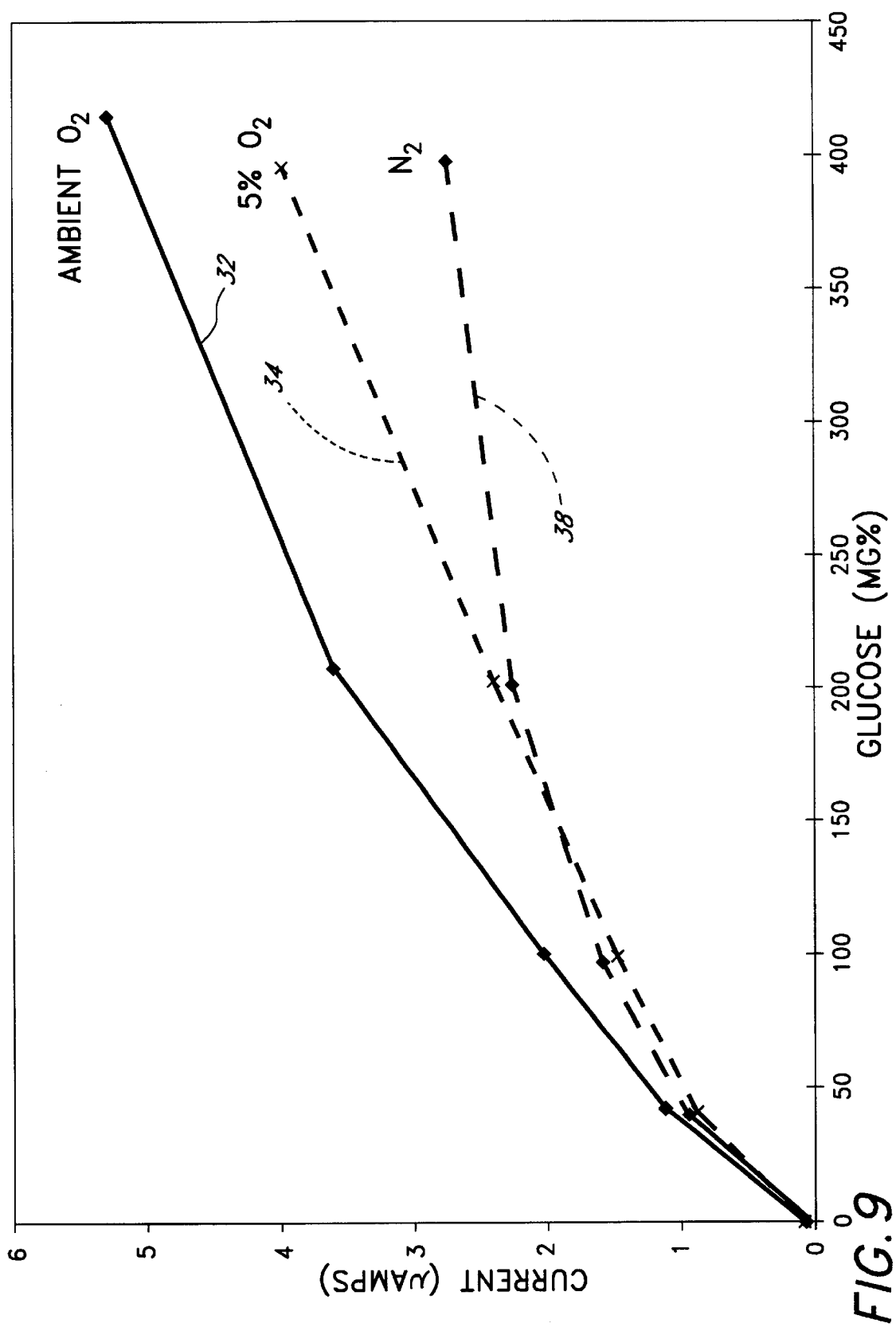
FIG. 9 shows the response of a stabilized enzyme emulsion containing 0.4% ferrocene to varying glucose concentrations at ambient oxygen concentrations, at 5% oxygen and at 0% oxygen (nitrogen atmosphere)

FIG. 9 shows the results of adding 0.4% by weight ferrocene to a stabilized enzyme mixture containing about 15% by weight BSA, 3.3% by weight glucose oxidase and about 0.6% glutaraldehyde. The ferrocene is dispersed into the buffer used to dissolve the glucose oxidase but does not appreciably dissolve therein. However, the ferrocene does affect the electrode response. Both the ambient oxygen trace 32 and the 5% oxygen trace 34 show a reasonably linear response to increasing glucose concentration, albeit at different slopes. Significantly, a 0% oxygen trace 38 (experiment performed under nitrogen) also shows some response to glucose. Thus, while the reaction is more pronounced in the presence of oxygen, the ferrocene is able to carry at least some electrons from the glucose oxidase to the electrode otherwise there would be no response at 0% oxygen.

Figure 10:
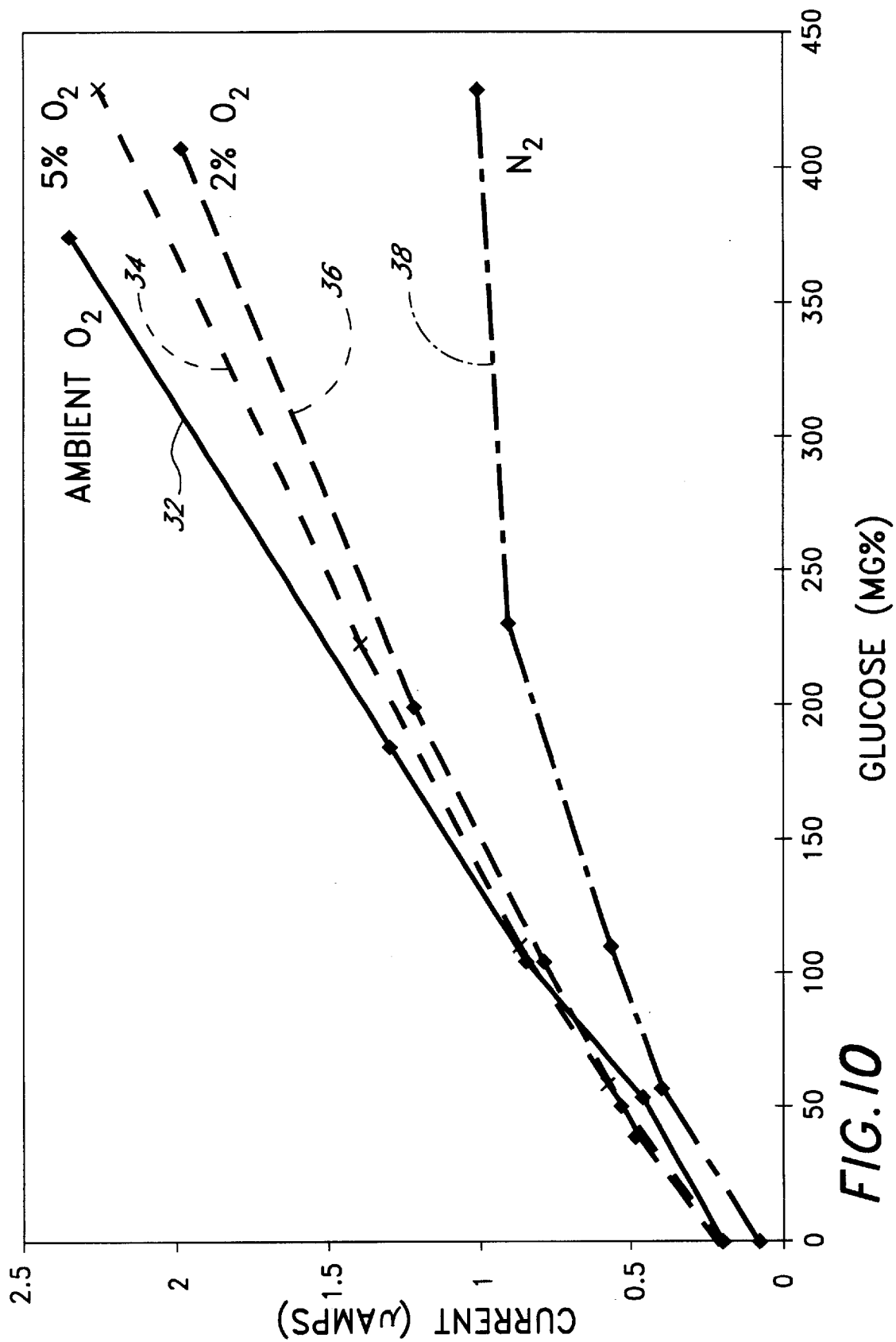
FIG. 10 shows the response of a stabilized enzyme emulsion containing a trace of ferrocene dissolved in 15% AP215 to varying glucose concentrations at ambient oxygen concentrations, at 5% oxygen at 2% oxygen, and at 0% oxygen (nitrogen atmosphere).

The present inventor has discovered that ferrocene (as well as certain ferrocene derivatives) is slightly soluble in perfluorocarbon liquids. Thus, it is possible to incorporate ferrocene directly into the perfluorocarbon-enzyme emulsion. FIG. 10 shows the results of incorporating ferrocene-containing perfluorocarbon into a stabilized enzyme emulsion. Here the enzyme mixture contained about 15% AP215, 12% BSA, 4% glucose oxidase and about 0.6% glutaraldehyde as a crosslinking agent. A quantity of ferrocene (less than 1% by weight) was added to the perfluorocarbon and allowed to dissolve overnight prior to sonicating the perfluorocarbon into the remaining ingredients. Enough ferrocene dissolves into the AP215 to color the liquid a light yellow. The intent is to saturate the perfluorocarbon with ferrocene.

Significantly, the ambient oxygen trace 32, the 5% oxygen trace 34 and the 2% oxygen trace 36 all show a linear response with surprising similar slopes. The 0% (nitrogen) trace 38 shows a much flatter response slope. This indicates that while the trace amount of ferrocene incorporated in the mixture does not carry as many electrons as does hydrogen peroxide, the perfluorocarbon plus ferrocene shows an unexpected synergistic activity superior to either ferrocene or perfluorocarbon alone. In some unknown way the ferrocene potentiates the effect of the emulsified perfluorocarbon particles.

The perfluorocarbon-insoluble enzyme mixtures of the present invention also permit other modifications that enhance the long-term stability and useful life of the implanted sensors. As mentioned above, premature failure of implanted electrodes has been attributed to free radical or oxidative damage to the enzyme. Therefore, addition of antioxidants or free radical trapping agents such as Vitamin E (tochopherols) can extend electrode life. Another problem that has troubled other research on implanted sensors is rejection of or immune reaction to the implant. As mentioned above, a fibroblast capsule often develops around an implant. This is, per se, not harmful, but the body may also mount a direct immune attack on the measuring membrane 19. This results in inflammation and proliferation of a large population of leukocytes in the vicinity of the membrane 19. Proliferating leukocytes can result in the release of "killing oxygen" wherein oxidative damage to the stabilized enzyme can occur. These white cells may consume considerable amounts of oxygen with their own respiration.

Even though the device of the present invention is preferably implanted at a site away from direct blood circulation to avoid problems caused by formation of blood clots, leukocytes can migrate out of the circulatory system to congregate around any "foreign" body. This leukocyte accumulation may damage the membrane and/or compromise the accuracy of the glucose readings. However, this problem can be largely avoided by incorporating an effective amount of an anti-inflammatory, anti-leukocyte compound into the enzyme mixture. One example is the addition of hydrocortisone, or similar cortical steroids such as cortisone and prednisone, at about 0.1 to 1.0% by weight. These steroids gradually dissolve in the aqueous phase of the enzyme mixture and very slowly diffuse out through the membrane 18 to keep the surrounding area free from attack by leukocytes (especially by macrophages). An advantage is that steroids, like perfluorocarbons, are much better at dissolving oxygen than is water.

In a series of experimental implants of titanium devices, similar to those of FIG. 1, in rats it was found that devices in which the enzyme mixture contained cortical steroids showed no evidence of inflammation. On the other hand, identical devices lacking cortical steroids showed significant evidence of inflammatory response when removed from the animals after six weeks.

Other non-steroidal anti-inflammatory drugs (i.e., aspirin, ibuprofen, naproxyn, ketoprofen and the like) or anti-inflammatory lymphokines or "anti-rejection" drugs (e.g., cyclosporine) may also be advantageously incorporated into the enzyme mixture. In addition, drugs that impede cell replication (e.g., "antineoplastic" agents) often have an advantageous effect in reducing inflammation and excess tissue proliferation. Useful agents include vinca alkaloids (vincristine and vinblastine), taxol derivatives and other well-known anti-tumor drugs.

Another serious impediment to long-term sensor implants is that of microbial contamination by bacteria and fingi, etc. While microbes may directly destroy the glucose-metabolizing enzyme, it is also likely for them to disrupt the glucose measurement by consuming glucose and oxygen or by producing catalase or peroxidase or other enzymes that consume the hydrogen peroxide before it can react with the electrode surface. The present inventor has found that the incorporation of antifungals or wide spectrum antibiotics into the enzyme mixture largely prevents microbial interference. For example, gentamycin and/or penicillin, and/or other broad-spectm antibiotics and antifungals (e.g., ketaconazole) can be incorporated into the enzyme mixture to prevent microbial growth. A relatively large concentration of antibiotic can be added so that sterility of the enzyme mixture is guaranteed for a long period of time. Slow diffusion of the antibiotic through the membrane keeps the entire area around the implanted sensor free of infection. Further, the electrode constantly produces hydrogen peroxide which is a powerful anti-infective agent.

The semipermeable membrane 19 is generally believed to protect the glucose oxidase from various proteases. However, in the experiments leading to the present invention, it was discovered that stabilized glucose oxidase is not readily attacked by a common proteolytic enzyme, trypsin. Apparently the chemical cross-linking that stabilizes the enzyme destroys the trypsin sensitive sites. Therefore, trypsin may be incorporated as an anti-proteolytic enzyme to help destroy other proteolytic enzymes that might be produced by microorganisms, etc.

Stability of the enzyme mixture of the present invention can also be improved by the addition of antioxidants and/or free radical trapping agents. Vitamin E, lycopene, and carotene which are also oxygen solvents, can be incorporated into the enzyme mixture as can any of a number of "preservatives" such as various parabens, BHT (butylated hydroxy-toluene) and its analogs, and/or superoxide dismutases. Further angiogenic factors can be added to ensure capillary growth and blood circulation near the sensor. Addition of an enzyme system to generate nitric oxide from arginine can be used to monitor microcirculation near the sensor. That is, arginine is injected into the patient's circulation, and a nitric oxide response by the sensor is indicative of adequate microcirculation.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. An implantable sensor for sensing a concentration of an organic substrate, the sensor comprising:
    a conductive electrode; and
    a stabilized enzyme emulsion in contact with the electrode, the enzyme emulsion comprising:
        an oxidase enzyme that quantitatively oxidizes the organic substrate;
        a water immiscible oxygen dissolving substance emulsified into intimate contact with the enzyme to provide oxygen; and
        a protein crosslinking agent to crosslink and insolubilize the enzyme forming a stabilized gel comprising crosslinked protein and particles of said oxygen dissolving substance.

2. The implantable sensor of claim 1 further comprising a semipermeable membrane covering the electrode with the enzyme emulsion sandwiched between the membrane and the electrode.

3. The implantable sensor of claim 1, wherein the enzyme emulsion also contains an additional carrier protein.

4. The implantable sensor of claim 3, wherein the additional carrier protein is selected from the group consisting of serum albumin and, gelatin.

5. The implantable sensor of claim 1, wherein the oxygen dissolving substance is selected from the group consisting of perfluorocarbons, silicone oils, fluorosilicone oils, aromatic and aliphatic hydrocarbon oils or solids, carotenoids and steroids.

6. The implantable sensor of claim 5, wherein the oxygen dissolving substance is a perfluorocarbon liquid selected from the group consisting of perfluorooctyl bromide, perfluorodichlorooctane, perfluorodecalin, perfluoroindane, perfluorophenanthrene, perfluorotetramethylcyclohexane, perfluoropolyalkylether oil, perfluoromethyldecalin, perfluorodimethylethylcyclohexane, perfluorodimethyldecalin, perfluorotrimethyldecalin, perfluoroisopropyldecalin, perfluoropentamethyldecalin, perfluorodiisopropyl decalin, perfluorodiethyldecalin, perfluoromethyladamantane, perfluorodimethyladamantane, perfluoro-di-xylethane, and perfluoro-6,7 H-undec-6-ene.

7. The implantable sensor of claim 1, wherein the crosslinking agent is selected from the group consisting of aldehydes, carbodiimides, imidoesters, pyrocarbonates, epoxides and N-hydroxysuccinimid esters.

8. The implantable sensor of claim 1, wherein the oxidase enzyme is selected from the group consisting of cholesterol oxidase, amino acid oxidase, alcohol oxidase, lactic acid oxidase, oxygen oxidoreductase, galactose oxidase, and glucose oxidase.

9. The implantable glucose sensor of claim 1 further comprising an electron transport compound dissolved in the water immiscible oxygen dissolving substance.

10. The implantable glucose sensor of claim 9, wherein the electron transport compound comprises ferrocene.

11. The implantable sensor of claim 1, wherein the enzyme emulsion further comprises an antioxidant.

12. The implantable sensor of claim 1, wherein the enzyme emulsion further comprises an antimicrobial agent.

13. The implantable sensor of claim 1, wherein the enzyme emulsion further comprises an anti-inflammatory agent selected from the group consisting of steroids, lymphokines, and non-steroidal anti-inflammatory drugs.

14. An implantable glucose sensor for sensing a concentration of glucose, the sensor comprising:
  a metal electrode; and
  a stabilized enzyme emulsion in contact with the electrode, the enzyme emulsion comprising:
    a solution of glucose oxidase protein for oxidizing glucose to quantitatively produce hydrogen peroxide;
    a perfluorocarbon liquid emulsified with the glucose oxidase; and
  a crosslinking agent to crosslink covalently said protein to form a stabilized gel comprising crosslinked protein and particles of the perfluorocarbon liquid.

15. The implantable glucose sensor of claim 14 further comprising a semipermeable membrane covering the electrode with the enzyme emulsion in contact with a first surface of the membrane and sandwiched between the membrane and the electrode and with body fluids or cells in contact with a second surface of the semi-permeable membrane.

16. The implantable sensor of claim 14, wherein the oxygen dissolving substance is a perfluorocarbon liquid selected from the group consisting of perfluorooctyl bromide, perfluorodichlorooctane, perfluorodecalin, perfluoroindane, perfluorophenanthrene, perfluorotetramethylcyclohexane, perfluoropolyalkylether oil, perfluoromethyldecalin, perfluorodimethylethylcyclohexane, perfluorodimethyldecalin, perfluorotrimethyldecalin, perfluoroisopropyldecalin, perfluoropentamethyldecalin, perfluorodiisopropyl decalin, perfluorodiethyldecalin, perfluoromethyladamantane, perfluorodimethyladamantane, perfluoro-di-xylethane, and perfluoro-6,7 H-undec-6-ene.

17. The implantable glucose sensor of claim 14 further comprising an electron transport compound dissolved in the perflurocarbon liquid.

18. The implantable glucose sensor of claim 17, wherein the electron transport compound comprises ferrocene.

* * * * *